US00PP37058P2

(12) United States Plant Patent
Hansoti

(10) Patent No.: US PP37,058 P2
(45) Date of Patent: Oct. 21, 2025

(54) ***SANSEVIERIA* PLANT NAMED 'Hansoti46'**

(50) Latin Name: *Sansevieria trifasciata*
Varietal Denomination: HANSOTI46

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,529

(22) Filed: Dec. 23, 2024

(51) Int. Cl.
*A01H 6/12* (2018.01)
*A01H 5/12* (2018.01)

(52) U.S. Cl.
USPC ..... Plt./382

(58) Field of Classification Search
USPC ..... Plt./382
CPC ..... A01H 6/12; A01H 5/12; A01H 5/02
See application file for complete search history.

*Primary Examiner* — Keith O. Robinson

(57) ABSTRACT

A new and distinct cultivar of *Sansevieria* plant named 'HANSOTI46' is disclosed, characterized by extra wide golden yellow borders on both sides of the leaf. Occasionally these can be wide enough to cover most of the leaf. The foliage is also characterized by vivid and distinct longitudinal bands and streaks of gold yellow along the length of the leaf lamina. Background color of the leaf is dark green, with almost none of the transverse banding typical of most *Sansevieria trifasciata* cultivars. The new cultivar can be classified in the Hahnii *Sansevieria* Group. The new variety is a *Sansevieria,* typically produced as an ornamental plant.

8 Drawing Sheets

Figure 1:
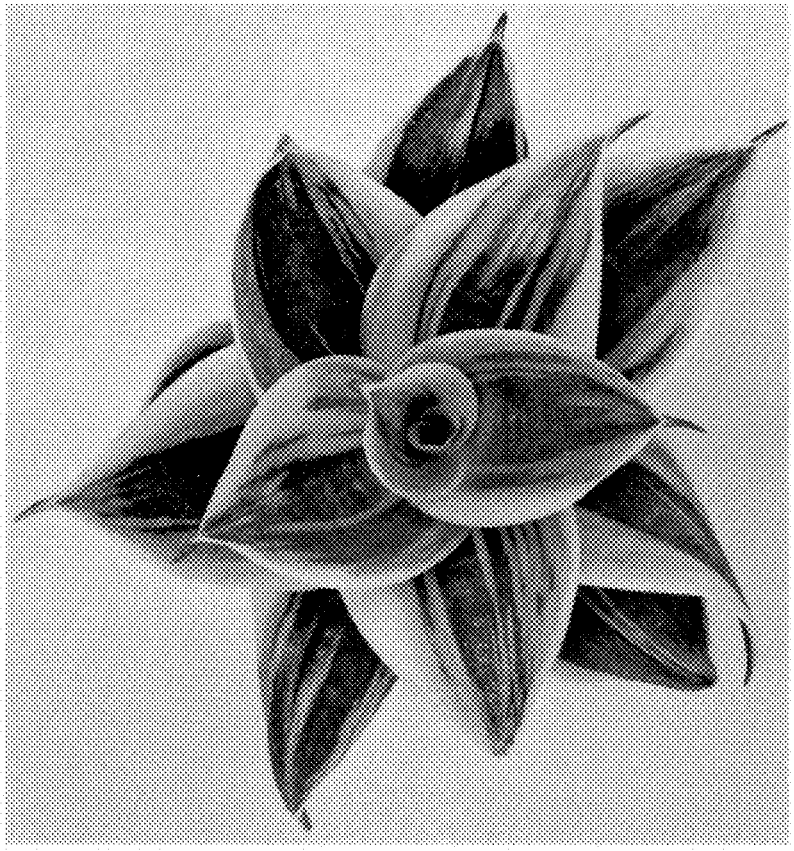

Latin name of the genus and species: *Sansevieria trifasciata.*

Variety denomination: 'HANSOTI46'.

BACKGROUND OF THE INVENTION

The present invention relates to a new and distinct cultivar of *Sansevieria* plant, botanically known as *Sansevieria trifasciata,* of the family Asparagaceae, hereinafter referred to by the cultivar name 'HANSOTI46'.

*Sansevieria* is a monocotyledonous plant with fleshy, succulent leaves which are available in a huge range of species, varieties and cultivars as an outdoor ornamental plant (under tropical conditions) or as indoor plants. Both, the parental of *Sansevieria trifasciata* 'Hahnii Marginata' and the new cultivar 'Hansoti46' belong to the group of *Sansevieria trifasciata* called "Hahnii *Sansevieria* Group" of very short or dwarf cultivars all ultimately derived from the original of *Sansevieria trifasciata* 'Hahnii' patented in 1941 (U.S. Plant Pat. No. 470), in contrast to the medium sized "Compact *Sansevieria* Group" with of *Sansevieria trifasciata* 'Futura Superba' (unpatented) as the typical example, and the "Tall *Sansevieria* Group" of *Sansevieria trifasciata* cultivars with tall leaves up to 4 feet (1.25 meters) or more and with of *Sansevieria trifasciata* 'Laurentii' (unpatented) as the typical example.

The new *Sansevieria* 'HANSOTI46' was discovered and selected by the inventor, Ashish Hansoti, as a single aberrant side shoot within a planting of *Sansevieria trifasciata* 'Hahnii Marginata', unpatented, a Hahnii type of *Sansevieria* grown at a nursery in Village Vangani, District Thane, Maharashtra State in Western India. 'HANSOTI46' originated as a naturally-occurring mutation of the *Sansevieria trifasciata* variety 'Hahnii Marginata' in May or June of 2020.

Asexual reproduction of the new *Sansevieria* cultivar by vegetative cuttings was first performed in early 2021 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI46', which in combination distinguish this *Sansevieria* as a new and distinct cultivar:

1. Extra wide golden yellow borders on both sides of the leaf. Occasionally these can be wide enough to cover most of the leaf.
2. Vivid and distinct longitudinal bands and streaks of golden yellow along length of the leaf lamina occurring randomly between these borders.
3. These are placed on a dark green background with almost none of the transverse banding typical of most *Sansevieria trifasciata* cultivars.
4. The broad borders and streaks in between combine to give the whole rosette a dark green look embellished with the bands and streaks giving a "flame-like" appearance to it, not unlike the old, medium sized Compact *Sansevieria* cultivar 'Gold Flame' (unpatented) but in a Hahnii Type form factor.
5. Overall, the rosettes of 'Hansoti46' are more compact than the parent—*Sansevieria trifasciata* "Hahnii Marginata" with smaller rosette diameter for plants of the same age/stage.

Leaf length is distinctly shorter and broader than in the parent cultivar, with leaves in typical 3-month-old plants being 11 to 13 cm long. Leaf width is quite variable and the strongest, healthiest plants have the widest leaves-this is true across all *Sansevieria trifasciata* cultivars known to the inventor. This variation means leaf width can be anything from 5 cm to 7 cm wide depending on season, growing conditions and plant vigour and plant age. Typically, the leaves are of medium width and lanceolate with a firm, waxy texture. The blades are stiff, thick and fleshy.

The new variety 'HANSOTI46' is a variety of *Sansevieria* in the group denominated as Birds Nest or Hahnii types based on its origin and overall plant form. The new variety presents with 10-13 mature leaves per plant when it reaches its saleable size (about 3 months from rooted cutting) but over time it can grow and accumulate many more leaves and increase in overall height.

The new variety is moderately drought tolerant and adapts well to conditions of bright light or heavy shade (exterior and interior). The intensity of leaf color varies with exposure to light and the contrast is most intense under high light conditions. The plant is liable to get scorched in full hot sun, especially under low humidity conditions.

The leaves show a variegated coloration, with dark green leaves with wide golden yellow borders but with the typical *Sansevieria trifasciata* cross hatching extremely subdued and hardly visible and, most prominently and uniquely, with randomly placed bands and streaks of golden yellow coloration along the length of the leaf, enhancing the brightness of the leaf.

Each leaf has a marginal yellow band of very variable width, but generally very broad, from 1 mm to 20 mm or more and is similar in color near R.H.S. Yellow-Green 154B. This golden yellow border is occasionally invaded with streaks of darker green from the central dark green area. This characteristic is also seen in its parental cultivar, *Sansevieria trifasciata* "Hahnii Marginata".

The central broad dark green area shows coloration similar to R.H.S. Greyed-Green N189A. This green expanse is invaded, quite randomly, by lines, bands and streaks of golden yellow running longitudinally along the length of the leaf. These characteristic golden yellow to greenish yellow bands and streaks are between Yellow-Green 144A and 144B and are randomly sized and placed anywhere between the two borders. Also, this yellow tissue occupies a variable depth within the leaf and this results in varying shades of golden yellow to greenish yellow. The usual transverse horizontal bands on the leaves (typically seen in most *Sansevieria trifasciata* cultivars) are almost entirely lacking The backside of the leaves has similar coloration to the front except that the typical *Sansevieria trifasciata* transverse horizontal banding is more obvious while the number of brighter yellow bands and streaks are reduced in number. The yellow border on the leaf edge varies greatly, but is still broad and varies from 2 mm to 20 mm or more.

Attached color pictures are a better guide to the complex leaf arrangement and the overall coloration and pattern rather than written descriptions.

PARENTAL COMPARISON

Plants of the new *Sansevieria* 'HANSOTI46' are similar to plants of the parental cultivar, however, 'HANSOTI46' differs in the characteristics described in Table 1.

TABLE 1

Comparison of Parental & the New variety 'Hansoti46'

| | Characteristic | Parent Cultivar 'Hahnii Marginata' | New cv 'Hansoti46' |
|---|---|---|---|
| 1. | Leaf size | 12 to 14 cm long | 11 to 13 cm long (Shorter leaves, more compact plants) |
| 2. | Number of leaves | 8 to 12 leaves | 10 to 13 leaves (More leaves) |
| 3. | Variegation Pattern | Cream border on dark green leaves with the typical *S. trifasciata* transverse banding very prominent. | Cream border on dark green leaves with randomly placed bands and streaks of light green/golden yellow. The typical *S. trifasciata* transverse banding is subdued. |
| 4. | Border variegation | 2 to 15 mm wide | 1 to 20 mm wide - usually much wider than in the parent |
| 5. | Central Variegation | Basic green background with distinct Transverse banding of lighter green as seen in most *S. trifasciata* cultivars. | Randomly distributed bands and streaks of lighter green/creamy yellow streaks on dark green background. Transverse banding indistinct. |

In essence, 'Hansoti46' is the old, familiar *Sansevieria trifasciata* 'Hahnii Marginata' with the addition of a prominent randomly placed creamy bands and streaks over whole of the leaf on a darker green background and with very subdued, barely seen cross-banding.

COMMERCIAL COMPARATOR

Plants of the new *Sansevieria* 'HANSOTI46' are similar to the commercial variety *Sansevieria trifasciata* 'Gold Flame', unpatented. Plants of the new *Sansevieria* 'HANSOTI46' differ from plants of the commercial cultivar in the characteristics described in Table 2.

TABLE 2

Comparison of similar old non-patented variety *S. trifasciata* 'Gold Flame' & the new variety 'Hansoti46'

| | Characteristic | Similar Cultivar *S. trifasciata* 'Gold Flame' | New cv 'Hansoti46' |
|---|---|---|---|
| 1. | Leaf size | 25 to 35 cm long | 11 to 13 cm long (Much shorter) |
| 2. | Number of leaves | 6 to 8 leaves (Fewer) | 10 to 13 leaves (More leaves) |
| 3. | Variegation Pattern | Variegation pattern is highly variable and changes with leaf age; mature, highly colored plants show large areas of golden yellow variegation on the leaves. Pattern is relatively random. Some transverse banding seen on top surface where the leaf is green but seen prominently on bottom surface. | Smaller, dark green leaves with creamy yellow border and randomly distributed bands and streaks of bright yellow. Transverse banding very subdued. |
| 4. | Border variegation | 2 to 12 mm wide golden band which, with increasing leaf maturity, expands to eventually cover most or entire leaf. Backside of leaf has more distinct yellow border. | 1 to 20 mm or even more wide golden yellow band on both sides of the leaf with barely seen, inconspicuous transverse banding. |

TABLE 2-continued

| Comparison of similar old non-patented variety *S. trifasciata* 'Gold Flame' & the new variety 'Hansoti46' | | | |
|---|---|---|---|
| | Charac-teristic | Similar Cultivar *S. trifasciata* 'Gold Flame' | New cv 'Hansoti46' |
| 5. | Central Variegation | Variegation typically starts as a small marking in center of the top half of the leaf and expands, in leaves with more maturity, to cover most of the leaf. In older plants under high light new leaves can come out almost entirely yellow gold. | Several streaks and bands of golden yellow along length of leaf on a dark green background with barely seen transverse banding. |

BRIEF DESCRIPTION OF THE PHOTOGRAPHS

The accompanying photographs illustrate the overall appearance of the new *Sansevieria* cultivar 'HANSOTI46' showing the colors as true as is reasonably possible with colored reproductions of this type. Colors in the photographs may differ slightly from the color value cited in the detailed botanical description which accurately describe the color of 'HANSOTI46'.

These pictures illustrate the plant form which is the unique characteristic of 'HANSOTI46' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 2:
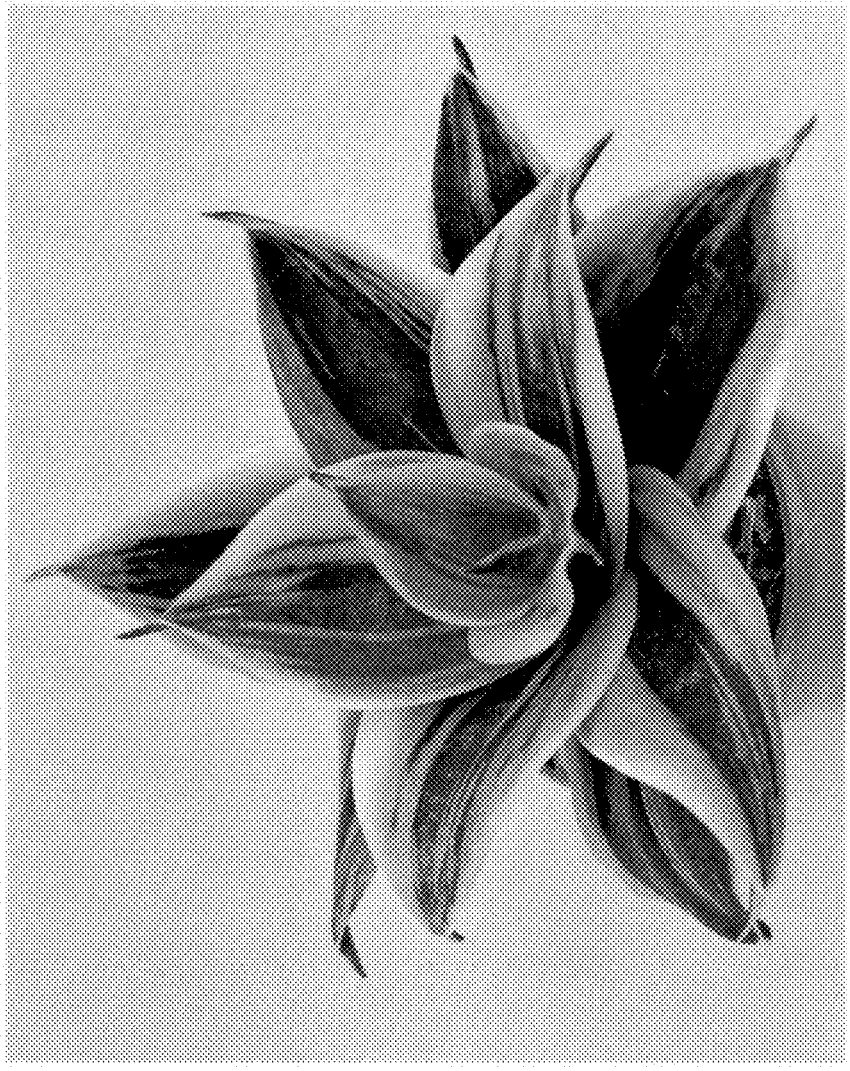
Figure 3:
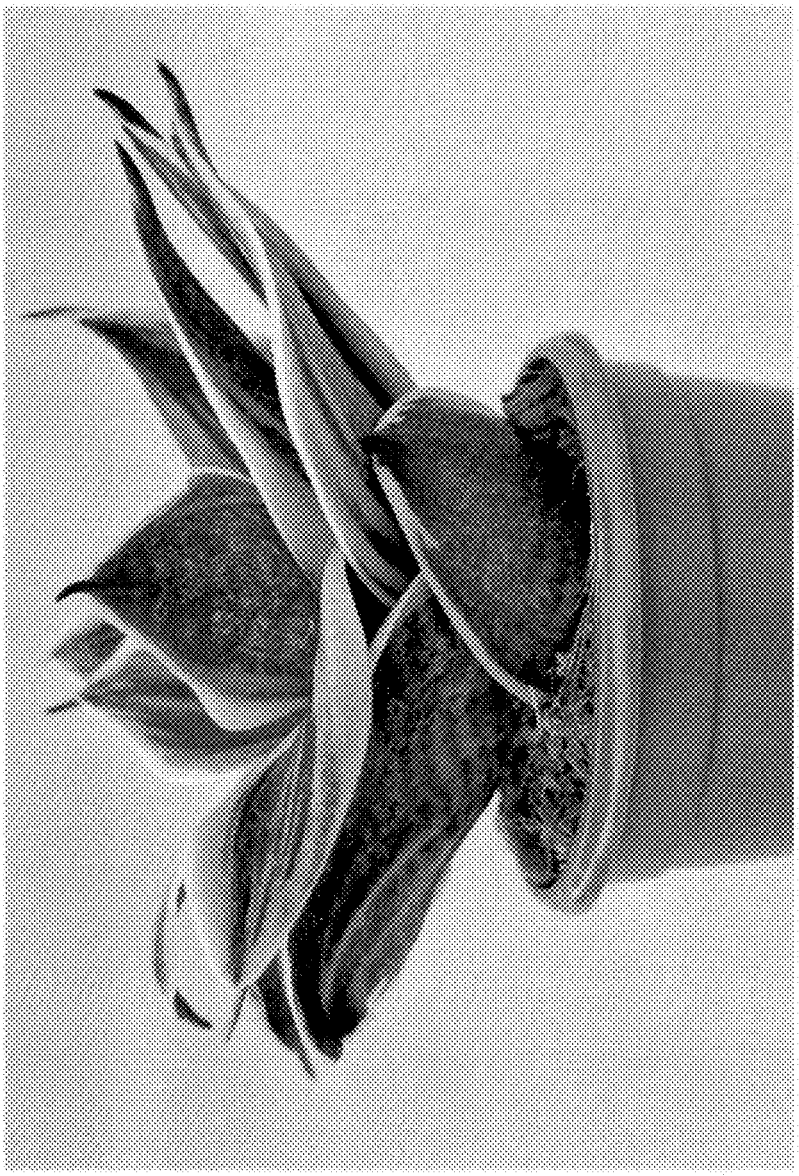

FIG. 1, FIG. 2 and FIG. 3: Show a three to four-month-old plant (from rooted liner) of *Sansevieria* 'Hansoti46' in a 12 cm diameter pot from various angles, showing top as well as bottom surface of leaves and leaf phyllotaxy.

Figure 4:
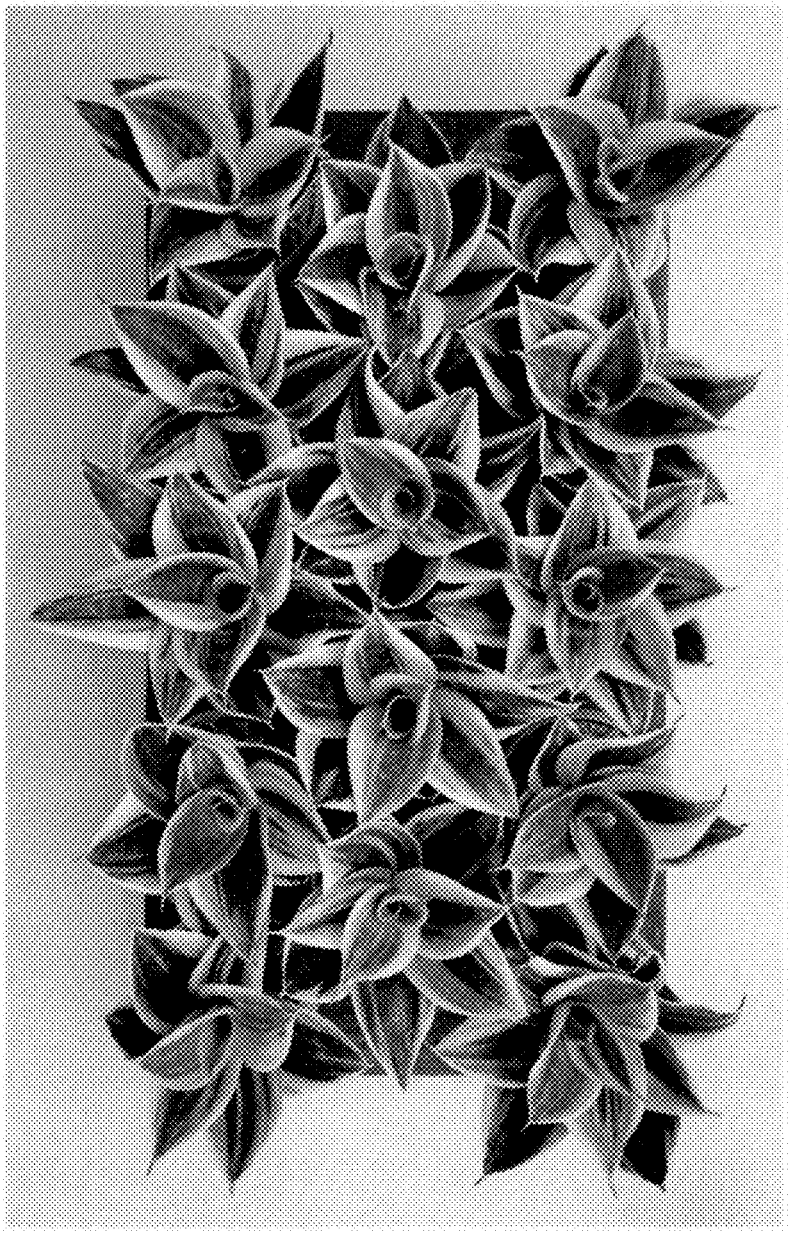

FIG. 4: Shows a group of 14 'Hansoti46' plants in a tray, showing uniformity of plant form and variegation across multiple plants of this new cultivar. These are in 10 cm pots. Plants are approximately 8 to 10 weeks old.

Figure 5:
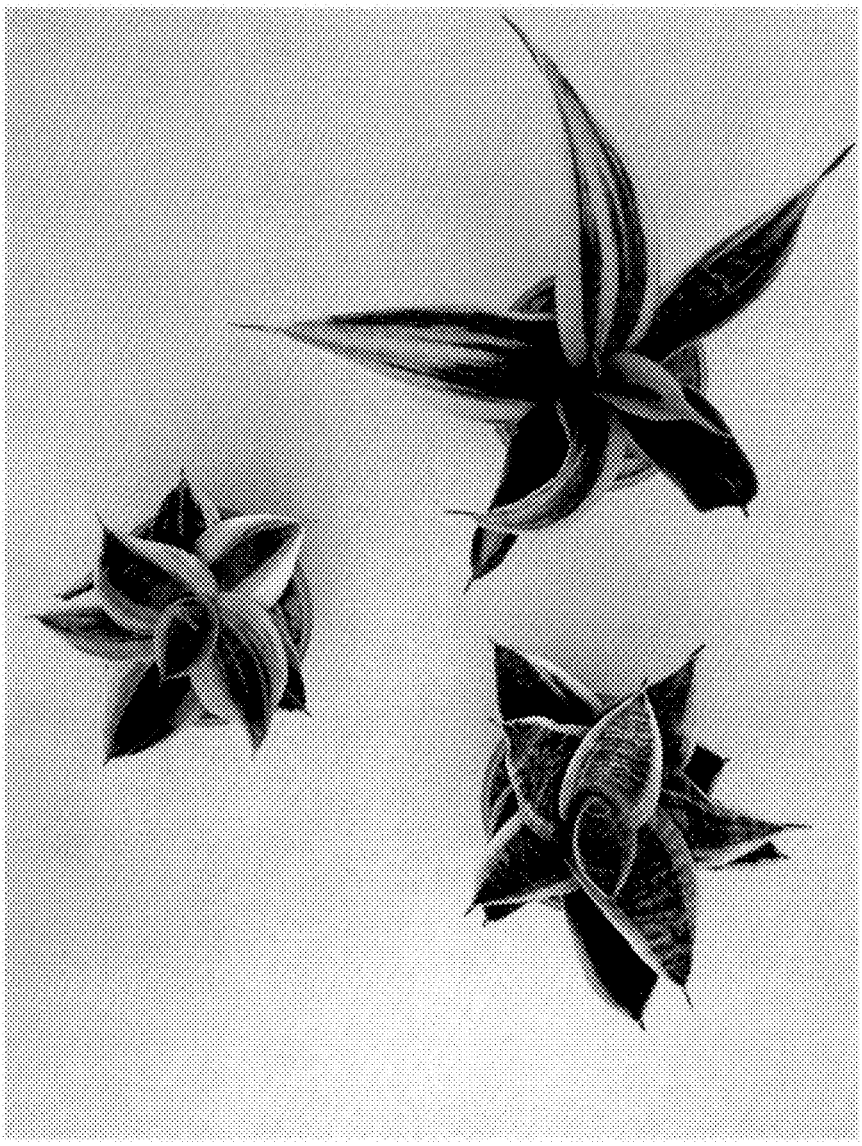
Figure 6:
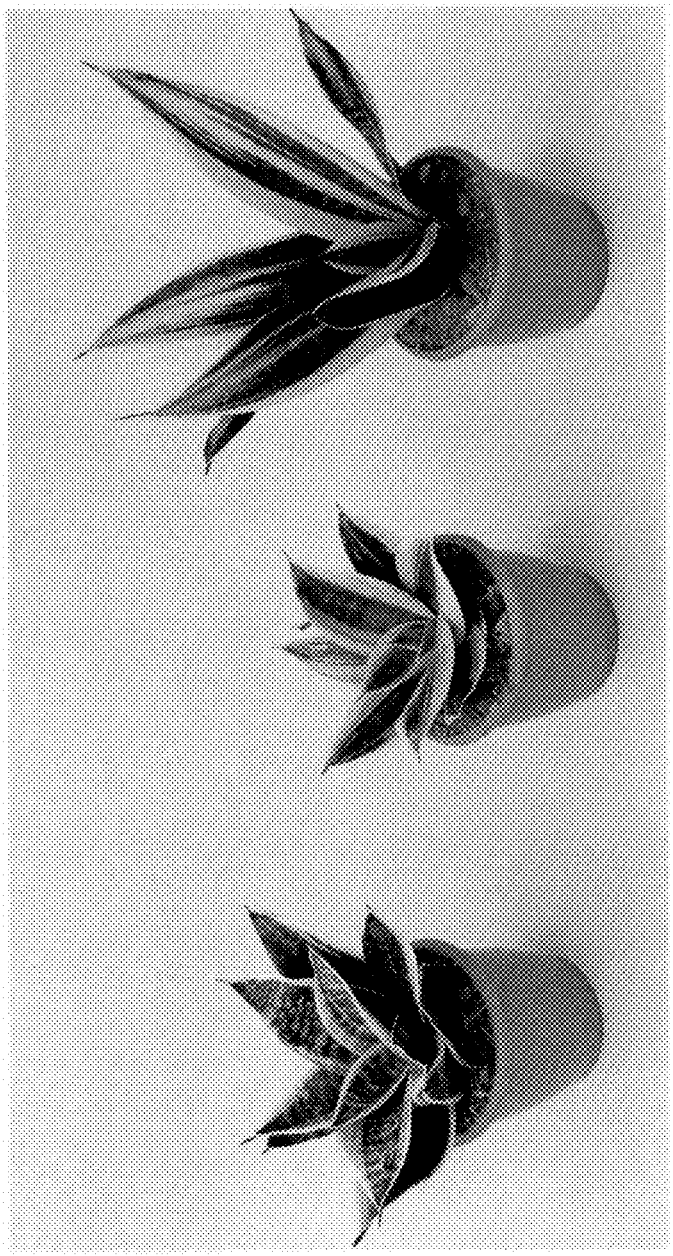

FIG. 5 and FIG. 6: Show the parent plant—*Sansevieria trifasciata* 'Hahnii Marginata' (lower left) as well as the other comparable variety *Sansevieria trifasciata* 'Gold Flame' (lower right)—alongside a plant of 'Hansoti46' (uppermost and middle) to compare the three, from two angels to show all aspects of the plants.

Figure 7:
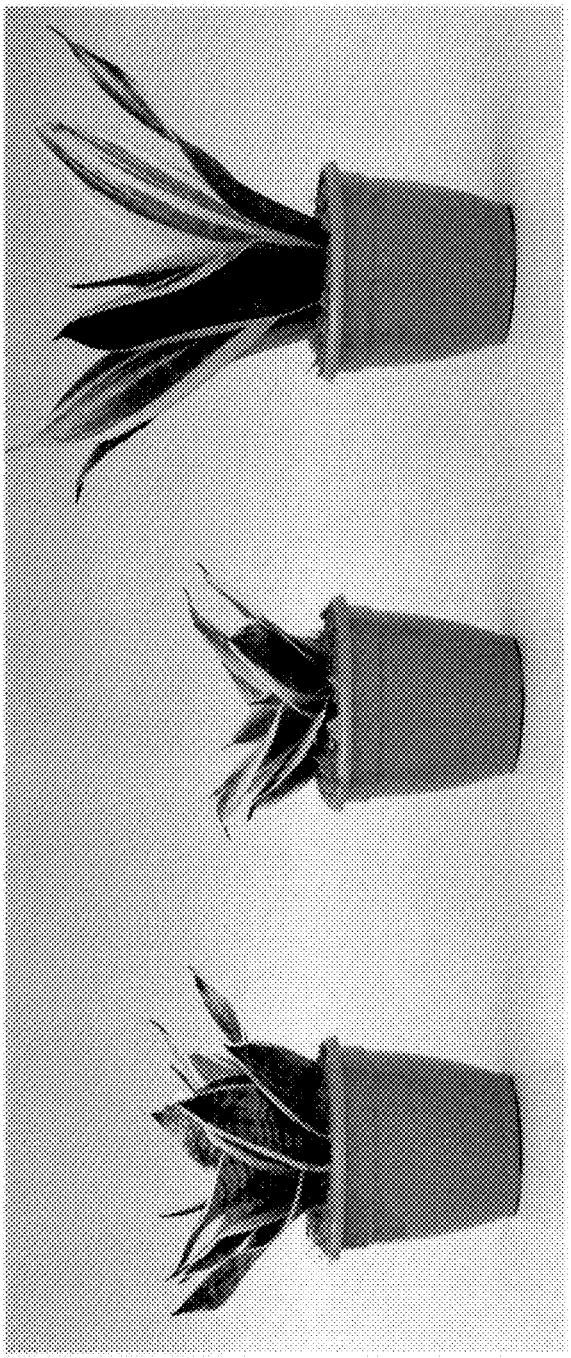

FIG. 7: Shows a comparison of abaxial surfaces of individual leaves of *Sansevieria* 'Hahnii Marginata' (left)-the parental variety-and the comparable variety *Sansevieria trifasciata* 'Gold Flame' (right) side by side with leaves of *Sansevieria* 'Hansoti46' (center)—the novel streaking in the center of leaves of 'Hansoti46' is very obvious.

Figure 8:
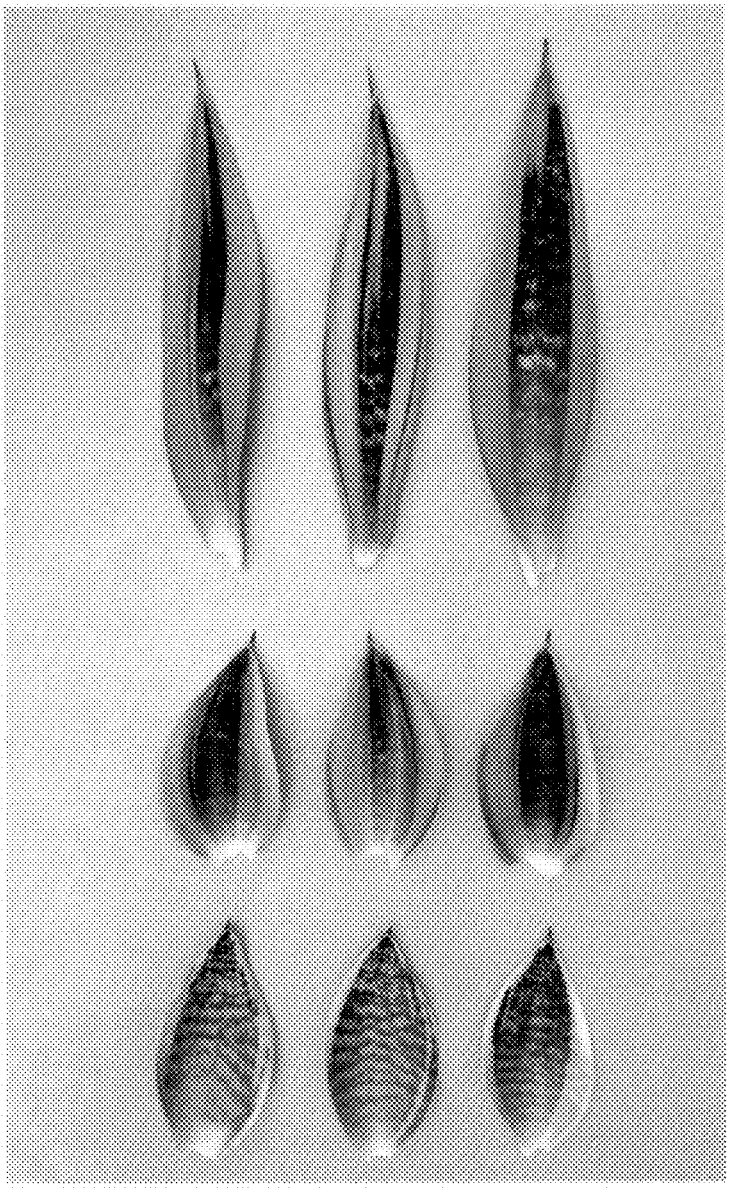

FIG. 8: Bottom or adaxial surface of individual leaves of *Sansevieria trifasciata* 'Hahnii Marginata'—the parental variety (Bottom row)—and leaves of the other comparable variety—*Sansevieria trifasciata* 'Gold Flame' (top row)—side by side with leaves of the new variety, *Sansevieria trifasciata* 'Hansoti46' (middle row).

DETAILED BOTANICAL DESCRIPTION

The new *Sansevieria* 'HANSOTI46' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI46' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer 13:11:11 Type 360-days release at 1 kilo/cubic meter of media, liquid fertilizer at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), (April 2007) except where general colors of ordinary significance are used. It should be noted that colors in *Sansevieria* are somewhat variable depending on light levels, nutrition balance, age of plant and other factors. The variety 'Hansoti46' has one major distinctive feature compared to its parent plant—a random number of lighter golden yellow/greenish yellow streaks running along the length of the leaf within the wide central green zone along with inconspicuous cross banding seen in most *Sansevieria trifasciata* cultivars—these streaks give an overall extra brightness to the plant not seen in the parent.

The photographs and descriptions were taken during the monsoon season in Asle, District Satara, Maharashtra State, India when outdoor day and night temperatures were 25° C. to 30° C. The age of the plants described is 3-4 months from rooted liners.

Botanical classification: *Sansevieria trifasciata* 'HANSOTI46'.

General information:

*Parentage.*—*Sansevieria trifasciata* 'Hahnii Marginata', unpatented.

*Optimal growth conditions.*—

*Light intensities.*—High adaptability to outdoor or indoor conditions but needs some shade in hot climates.

*Temperature.*—Day: 25° C. to 35° C. Night: 15° C. to 25° C.

*Temperature tolerance.*—Tolerant to a low temperature of about 6° C. and a high temperature of 39° C. and above-very heat tolerant.

*Fertilization.*—Constant feed of 100 ppm N, 20 ppm P and 100 ppm K is used along with micronutrients with occasional leaching. Media incorporation of 13:11:11 Type 360 days release at 1 kg/cubic meter of media.

*Growth regulators.*—Not necessary for growth, however rooting hormone aids in rapid and prolific rooting of offsets.

Propagation:

*Typical.*—Vegetative, by side suckers which come true to type. Does not come true from leaf cuttings.

*Rooting habit and description.*—Rhizomes are elongated, fleshy, giving rise to offsets (side shoots).

Offsets root easily with fibrous adventitious roots from cut end. Rooting hormone helps in faster and more prolific rooting. Colored cream to brown, not accurately measured with R.H.S. chart.

*Time to initiate roots.*—25 to 30 days at 25° C. to 30° C.

*Time to produce a rooted liner.*—About 45 days at 25° C. to 30° C.

*Time to produce ready* 12 *cm potted plant from liner.*—About 10 to 12 weeks at 25° C. to 30° C.

Plant:

*General appearance and form.*—Monocot; leaf bases arranged in a rosette around growth point.

*Height.*—About 12 to 14 cm when grown in 12 cm pots.

*Spread.*—About 18 to 22 cm when grown when grown in a 12 cm size container.

*Growth rate and habit.*—Moderate growth rate, stays flat and compact.

*Shape.*—Rosette.

*Fragrance.*—None.

*Stem.*—Modified (rhizomes which are fleshy with erect foliage, branching and giving offsets so forming clumps in time).

*Rosette height.*—About 12 to 14 cm height from top of pot when grown in 12 cm size container.

*Rosette diameter.*—About 18 to 22 cm.

*Texture.*—Smooth, waxy.

*Strength.*—Strong and durable.

*Internode length.*—About 1 mm.

Foliage:

*Quantity.*—About 12 to 14 in ready to sell plant. Number slowly increases with age.

*Arrangement and attachment.*—Single, alternate; leaf bases arranged stiffly in a rosette around central growth point.

*Leaf length.*—About 11 to 13 cm, full-size leaf.

*Leaf width.*—About 5 to 7 cm, full-size leaf.

*Overall shape of leaf.*—Lanceolate.

*Apex shape.*—Acute, triangular and aristate, with soft tip.

*Base shape.*—Plane.

*Margin.*—Sharp, smooth.

*Texture.*—Upper Surface: Smooth and waxy texture.

*Texture.*—Under Surface: Smooth and waxy texture.

*Pubescence.*—None.

*Color of mature leaf, upper surface.*—Basal dark green color near R.H.S. Green N189A with broad yellow border close to Yellow-Green 154B, subdued transverse banding of Greyed-Green 193A and central wide green zone with streaks of Greyed-Green N144C.

*Margins.*—Golden yellow near R.H.S. Yellow-Green 154B.

*Crossbanding.*—Typical crossbanding as seen in most *Sansevieria trifasciata* cultivars is subdued, with color near R.H.S. Greyed-Green 193A.

*Color of mature leaf, lower surface.*—Much more prominent transverse banding with narrower dark bands of R.H.S. Greyed-Green N189A and broader lighter bands of Greyed-Green 193A. The longitudinal yellow bands so prominent and characteristic on the top surface are somewhat subdued on the bottom surface, Yellow-Green 145C). Margin: the edge band is thinner, less prominent but same color as the top surface.

*Venation pattern.*—Longitudinal/parallel leaf shape.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs (*Rhizoecus pritchardi*). Typical pests include *Pseudococcidae longispinus* and *Tetranychus urticae.*

*Disease resistance.*—Occasionally shows *Anthracnose* and leaf spots but largely disease-free from clean mother stock and appropriate disease mitigation measures undertaken.

*Fruit/seed production.*—No fruits/seeds detected to date.

What is claimed is:

1. A new and distinct cultivar of *Sansevieria* plant named 'HANSOTI46' as herein illustrated and described.

* * * * *